United States Patent [19]

Meier et al.

[11] 4,143,652

[45] Mar. 13, 1979

[54] SURGICAL RETAINING DEVICE

[76] Inventors: Hans Meier, Bahnhofstrasse 13, 5507 Mellingen; Jaroslav Dbaly, Jupiterstrasse 55, 3015 Bern, both of Switzerland

[21] Appl. No.: 762,140

[22] Filed: Jan. 24, 1977

[30] Foreign Application Priority Data

Jan. 29, 1976 [CH] Switzerland ............... 1099/76

[51] Int. Cl.² ................................ A61B 17/02
[52] U.S. Cl. ............................................ 128/20
[58] Field of Search ....................... 128/20, 132 D

[56] References Cited

U.S. PATENT DOCUMENTS

| | | | |
|---|---|---|---|
| 2,608,192 | 8/1952 | Heitneyer et al. | 128/20 |
| 3,046,072 | 7/1962 | Douglass et al. | 128/20 X |
| 3,823,709 | 7/1974 | McGuire | 128/132 D |
| 3,910,538 | 10/1975 | Baitella | 248/122 |

FOREIGN PATENT DOCUMENTS 1235135  5/1960  France .............................. 128/20

OTHER PUBLICATIONS

Gardlock retractor mitten, MSR Oct.-Nov. 1971, p. 47.

*Primary Examiner*—Robert W. Michell
*Assistant Examiner*—Michael H. Thaler
*Attorney, Agent, or Firm*—Werner W. Kleeman

[57] ABSTRACT

A surgical retaining device for holding a surgical instrument in place, typically wound hooks, comprising a holder block for displaceably securing the surgical retaining device at a stationary object and at least one insert element into which there can be inserted and fixedly clamped the surgical instrument. Between the insert element and the holder block there is arranged a double-arm pivotable stand possessing an intermediate pin joint. The pivotable stand is connected at one end by means of a ball-and-socket joint at the insert element and at its other end by means of a further ball-and-socket joint with an overhang arm which can be fixedly clamped at random elevational and angular positions with respect to the holder block at the latter.

8 Claims, 13 Drawing Figures

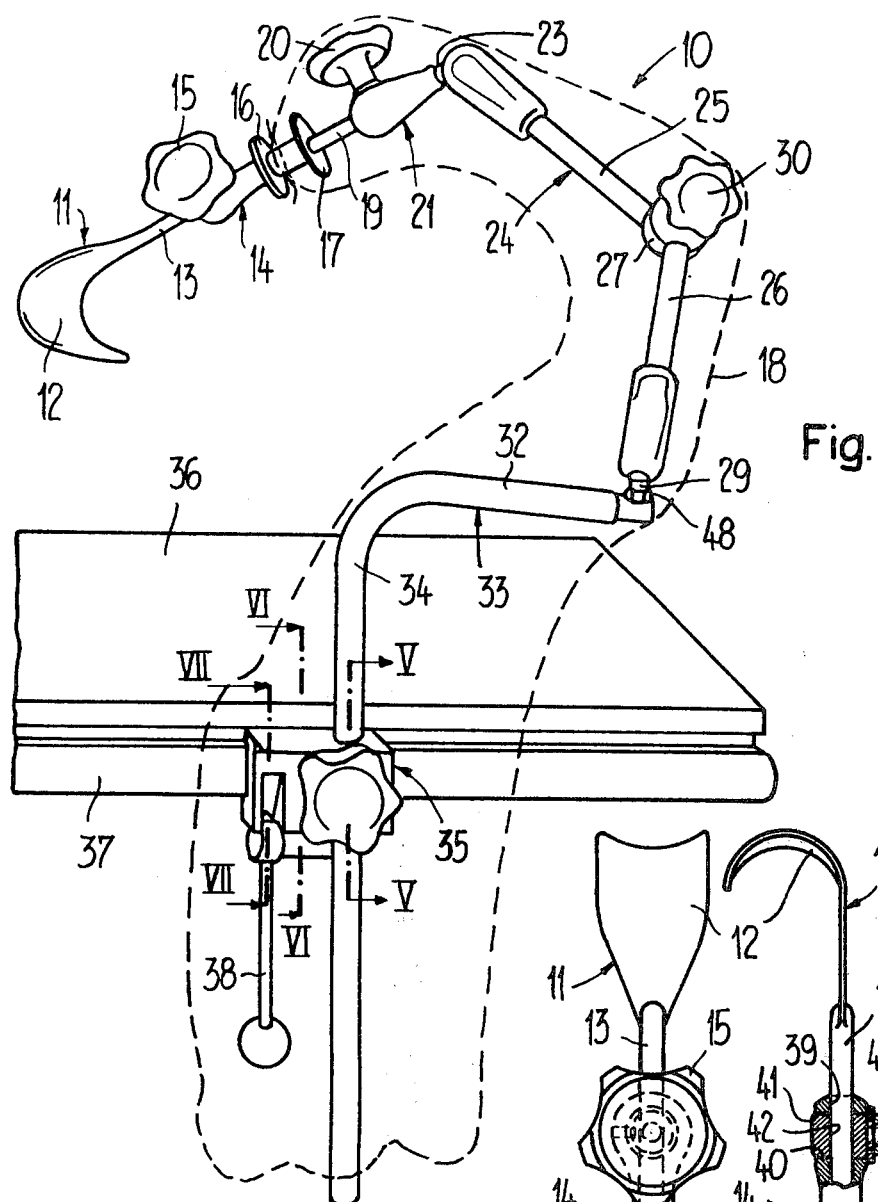
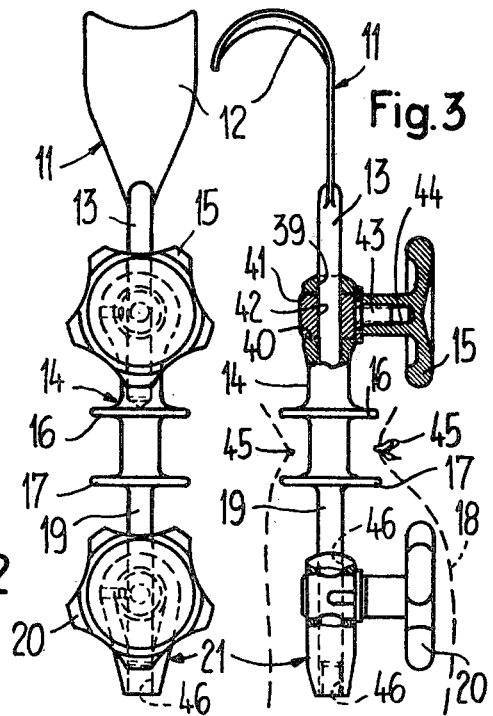

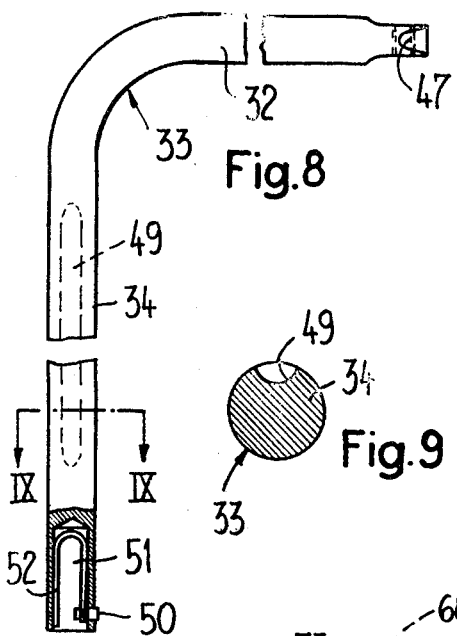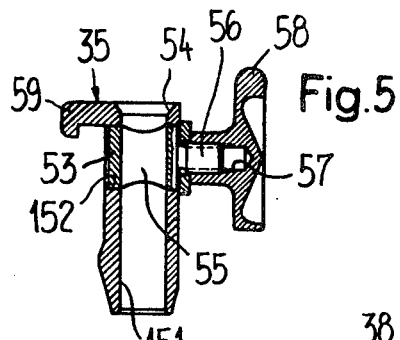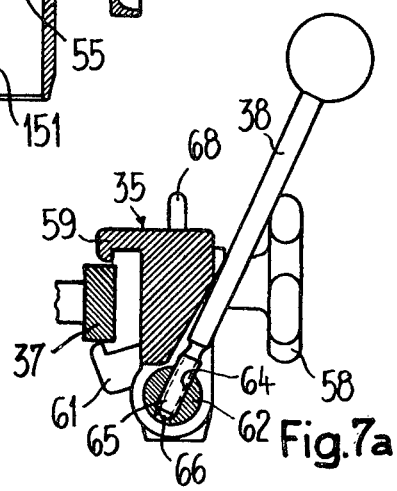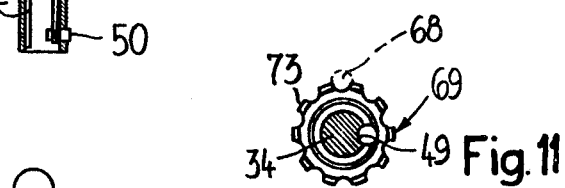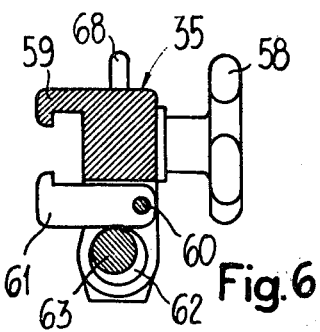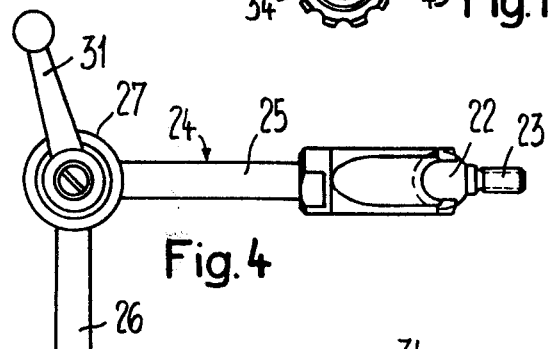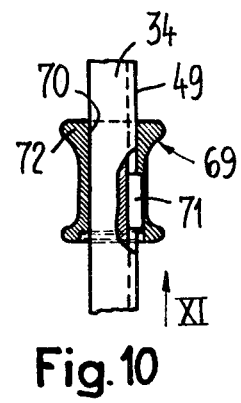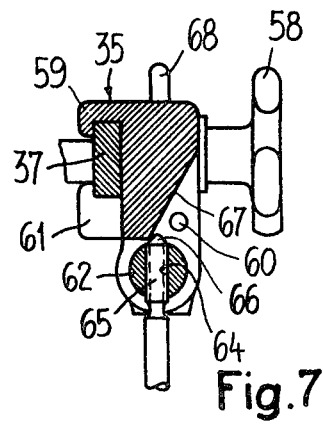

SURGICAL RETAINING DEVICE

BACKGROUND OF THE INVENTION

The present invention relates to a new and improved construction of a surgical retaining or holder device for holding a surgical instrument in place, especially although not exclusively wound hooks, which is of the type comprising a holder block serving for the displaceable attachment of the holder device at a stationary object and at least one insert element at which there can be inserted and fixedly clamped the surgical instrument, wherein the holder block and the insert element are coupled with one another by a number of lockable or blockable joints.

In the context of this disclosure the expression "surgical instruments" not only encompasses the aforementioned wound hooks, but also other surgical instruments, such as, for instance, speculars for the most different purposes as well as wound spreaders, magnifying lenses, spatulas, holders for X-ray plates or cassettes and similar instruments, which enable the surgeon to carry out or perform more easily his work.

In U.S. Pat. No. 3,858,578 as well as in German petty Pat. Nos. 6,941,781 and 7,010,461 there have been disclosed to the art such type of surgical retaining or holder devices. With the prior art holder devices there is provided a flexible link arm between the insert element and the holder block. This link arm is composed of a multiplicity of link elements possessing at one end a ball and at the other end a complementary ball socket. The link elements, in turn, are threaded, in the manner of pearls upon a string of pearls, onto a flexible traction element. At the neighborhood of the holder block the traction element is connected with a clamping device (in U.S. Pat. No. 3,858,578 such is constituted by a pneumatic cylinder and in the aforementioned German petty patents there are provided clamping screws), by means of which there can be tightened the traction element, so that the link arm which is composed of practically a multiplicity of ball-and-socket joints which are arranged in a row is caused to assume a rigid structure i.e., can be arrested in any position selected by the surgeon or other user of the device.

In practice it has been found, however, that the state-of-the-art surgical retaining or holder devices are not capable of positionally fixing larger wound hooks with adequate retention force, such as for instance would be necessary when performing more complicated operations, such as for thorax or abdominal surgery, in order to fix with the requisite security the edges of the wound in position. This is not overly surprising if it is recognized that with a single traction element (irrespective of its unavoidable elongation) it is hardly possible to increase the friction at each of the multiplicity of ball-and-socket joints to such an extent that the link arm can be in fact transformed into a rigid structure. This difficulty in attaining a sufficient retention force with the heretofore known holder devices has also resulted in restricting their practical use in surgery to those instances where the surgeon is working in a relatively small operating zone, for instance, for neurological surgery.

Additionally, the prior art surgical retaining or holder devices are associated with a further disadvantage inasmuch as the end of the link arm supporting the insert element, upon tightening of the traction element, has the tendency of slightly shifting out of the position selected by the surgeon. Finally, it is also to be mentioned that the multi-element link arm constitutes a structure which can only be sterilized with considerable effort.

SUMMARY OF THE INVENTION

Therefore, in view of the foregoing it is a primary object of the present invention to provided a new and improved construction of surgical retaining device which is not associated with the aforementioned drawbacks and limitations of the prior art constructions.

Another and more specific object of the present invention aims at the provision of a new and improved construction of surgical retaining or holder device of the previously mentioned type, which while completely retaining the freedom of movement of the insert element enables, following locking of the joints, establishment of a considerably greater retaining or holding force.

Still a further significant object of the present invention is to provide a surgical retaining device which is relatively simple in construction and design, economical to manufacture, easy to use and sterilize, and enables the surgeon or other user of the device to fix in a reliable manner a surgical instrument in a desired postion.

Now in order to implement these and still further objects of the invention, which will become more readily apparent as the description proceeds, the surgical retaining or holder device of the present invention is manifested by the features that a double-arm pivotable stand having an intermediate pin joint is arranged between the insert element and the holder block. The pivotable stand is articulated at one end by means of a ball-and-socket joint at the insert element and at the other end by means of a further ball-and-socket joint at an overhang arm which, in turn, can be fixedly clamped at the holder block in random elevational and angular postions relative thereto.

The surgical retaining or holder device thus can be compared to a human arm, wherein the ball-and-socket or universal joints constitute the shoulder and wrist joint and the pin joint the elbow joint. The presence of only three joints or hinges increases the obtainable degree of rigidity of the holder device.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 1 is a perspective view of a surgical retaining or holder device shown mounted at an operating table;

FIG. 2 is a side view of the surgical instrument clamped by means of its shaft at the clamping head of the surgical retaining device;

FIG. 3 is an end view, partially in section, of the arrangement of FIG. 2;

FIG. 4 is a side view of the pivotable stand of the surgical retaining device;

FIG. 5 is a cross-sectional view through the holder block shown in FIG. 1 taken substantially along the line V—V thereof;

FIG. 6 is a cross-sectional view through the holder block shown in FIG. 1 taken substantially along the line VI—VI thereof;

FIGS. 7a and 7b are respective cross-sectional views through the holder block illustrated in FIG. 1 taken substantially along the line VII—VII thereof, and depicting the illustrated structure in different operating positions;

FIG. 8 is a side view of an angle member used in the surgical retaining device of the present invention;

FIG. 9 is a cross-sectional view of the arrangement of FIG. 8 taken substantially along the line IX—IX thereof;

FIG. 10 is a sectional view of a sleeve, not shown in FIG. 1, which is displaceable along the vertical leg of the angle member and used for fixing the angular or rotational position of the angle member with respect to the holder block;

FIG. 11 is a view of the sleeve shown in FIG. 10, looking in the direction of the arrow XI.

DETAILED DESCRIPTION OF THE PREFERRED EMBODIMENTS

Figure 12:
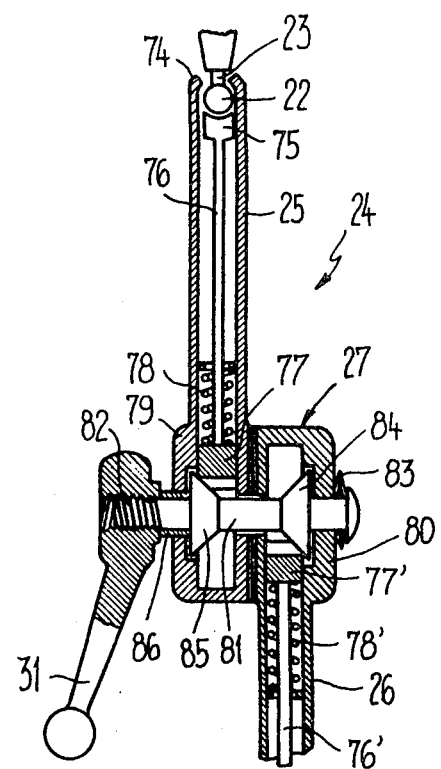
FIG. 12 is a schematic longitudinal sectional view through part of the pivotable stand of the surgical retaining or holder device.

Describing now the drawings, it is to be understood that based upon the showing of FIG. 1 initially there will be described only the more important components of the surgical retaining or holder device of the invention, which has been generally designated by reference character 10. A surgical instrument, here shown by way of example in the form of a wound hook 11 having a blade 12 and a shaft 13, is clamped by means of such shaft in a clamping or fixing head 14. The clamping head 14 possesses a rapid clamping device, details of which will be described more fully hereinafter, and which can be operated by means of a handwheel 15 or equivalent structure. Flanges 16 and 17 are provided in spaced relationship from one another at the clamping head 14. One of the purposes of the flanges 16 and 17 is to attach a hood member or cover 18, composed of for instance sterilized fabric, this cover or hood member, when used, covering the entire device with the exception of the clamping head 14 and the wound hook 11 or other surgical instrument.

The shaft 19 of the clamping head 14 is likewise clamped by means of a rapid clamping device in an end or terminal piece 21, which rapid clamping device can be actuated by means of the handwheel 20. The end piece 21 in turn is threaded at a bolt 23 protruding from a ball 22 (FIG. 4).

The ball 22 is part of a ball-and-socket joint located at one end of a pivotable stand 24 or the like, which possesses two rods 25 and 26 articulated to one another by means of a pin joint or hinge 27 or equivalent structure. At the other end of the pivotable stand 24 there is likewise provided a ball-and-socket joint embodying a ball 28 and a bolt or pin 29 formed thereat. Further details of an exemplary arrangement of such stand 24 will be apparent from FIG. 12. It should be sufficient to note at this point that all three joints or hinges of the pivotable stand 24, i.e. both of the ball-and-socket joints as well as the pin joint 27 provided between the rods 25 and 26 can be arrested in position and released by means of a single handwheel 30 (FIG. 1) or a single clamping lever 31 (FIG. 4).

The bolt 29 is threaded into the free end of one leg 32 of a substantially gallows-shaped angle member 33 providing overhang arm means, the other leg 34 of which extends through a holder block 35 and at that location is releasably fixed in both its elevational position as well as angular position. The leg 32 can be considered to constitute an overhang leg and the other leg 34 a vertically extending leg of the angle member 33.

Continuing, it is to be recognized that the holder block 35 in turn engages with a rail 37, for instance possessing a substantially T-shaped cross-section, which is secured at the side of a stationary object, for instance an operating table 36. Holder block 35 can be fixedly clamped into its randomly selected displaced position at the rail 37 by means of a lever 38 or other equivalent expedient.

From what has been discussed above it will be apparent that only the surgical instrument e.g. wound hook 11 and the clamping head 14 are directly accessible to the surgeon, whereas all other parts which can be operated are accessible only however through the hood member or cover 18. Therefore, it is only necessary to maintain in a sterilized condition the parts 11, 14 and 18, and thus it is unnecessary to sterilize the joints which otherwise only could be sterilized with difficulty.

In FIGS. 2 and 3 the wound hook 11 and the clamping head 14 have been illustrated. The shaft 13 of the wound hook 11 is substantially cylindrical in shape and fits into an axial bore 39 provided in the clamping head 14. This clamping head 14 is also equipped with a transverse bore 40 of enlarged diameter in which there is displaceably but non-rotatably arranged a thrust sleeve 41. This thrust sleeve 41 in turn is equipped with a transverse bore 42 having the same diameter as the bore 39. Furthermore, at the thrust sleeve 41 there is formed a bolt 43 upon which there is threaded the handwheel 15 equipped with a nut thread 44. If the bores 39 and 42 are exactly aligned in succession i.e., coaxially positioned, then the wound hook 11 can be easily retracted out of the clamping head 14. A slight rotation of the handwheel 15 is sufficient to displace the thrust sleeve 41 to such an extent that there is eliminated the unavoidable play between the bore 39 and 42 on the one hand and the shaft 13 on the other hand and to fixedly clamp such shaft. Also it will be appreciated that no considerable tightening force must be applied to the handwheel 15.

Furthermore, FIGS. 2 and 3 illustrate the flanges 16 and 17, and there has been shown a possibility of attaching the hood 18 by means of a draw string 45 between such flanges 16 and 17, so that such hood is not able to shift along the clamping head 14 either in the one or in the other direction.

The shaft 19 of the clamping head 14 extends into an axial bore 46 provided at the end piece 21 and is clamped at that location in a manner analagous to the clamping of the shaft 13 at the clamping head 14. Thus, also the clamping head 14 together with the wound hook 11 can be removed from the end piece 21. This is necessary on the one hand because both the wound hook 11 as well as also the clamping head 14 must be sterilized in conventional manner since such elements, when the surgical retaining device is used, are directly accessible. On the other hand, this possibility of removing such components affords the additional advantage that, if necessary, and for a shorter period of time the clamping head 14 also can be used as a hand grip for an instrument which is being manipulated, for instance for the wound hook 11 or another similar wound hook or surgical instrument, and such "hand grip" which is provided for emergencies can serve to handle an entire set of different blades or hooks.

The end piece 21 is provided at its lower end with internal threading 46, by means of which such end piece 21, as already mentioned, can be threaded to the bolt 23 of the ball 22. In order to secure such connection there can be further provided a not particularly illustrated counter or retaining nut member or equivalent structure. As mentioned, the ball 22 constitutes part of the ball-and-socket joint at the one end of the pivotable stand 24.

The bolt 29 formed at the ball 28 at the other end of the stand 24 is threaded into a threaded bore 47 (FIG. 8) provided at the end of the leg 32 of the angle member 33. Also this threaded connection is secured by means of a counter or retaining nut member 48 (FIG. 1) or equivalent structure. At its outer surface the leg 34 of the angle member 33 is provided with a longitudinal or lengthwise extending groove 49 which has an approximately semi-circular cross-sectional configuration. The purpose of this longitudinal groove 49 will be explained more fully hereinafter in conjunction with the description of FIGS. 10 and 11. Moreover, at the free end of the leg 34 there is provided a radially protruding impact or stop knob 50, constituting stop means, which itself can be pushed into the leg 34 against the action of a leaf or blade string 52 or the like arranged in a bore 51. The impact or stop knob 50 prevents, during elevational positioning of the angle member 33, that the leg 34 thereof will be unintentionally retracted out of the associated bore provided in the holder block 35.

Different sectional views through the holder block 35 have been shown in FIGS. 5, 6, 7a and 7b. By referring to FIG. 5, it will be seen that in the holder block 35 there is provided a bore 151 equipped with a countersunk portion 54 and serving to receive the leg 34 as well as a transverse bore 152 extending transversely with respect to the bore 151. Just as was the case for the clamping head 14, in this transverse bore 152 there is displaceably, yet non-rotatably arranged a thrust sleeve 53 which in turn possesses a longitudinal bore 55, the diameter of which corresponds to the diameter of the bore 151. Formed at the thrust sleeve 53 is a threaded bolt 56 upon which there is threaded a handwheel 58 equipped with a nut thread 57 or the like. The leg 34 of the angle member or element 33 can be easily introduced into the bore 151, and the countersunk portion 54 insures that the impact or stop knob 50 will be sunk or retracted until the end of the leg 34 departs from the lower end of the bore 151. By means of the handwheel 58 it is additionally possible to immovably fixedly clamp the leg 34 in a random elevational position. From the showing of FIG. 5 it will be furthermore seen that a flange 59 is formed at the holder block 35, this flange in the assembled condition engaging from above over the rail 37 provided at the operating table 36.

As best seen by referring to FIG. 6, as the counter-element for the flange 59 there is provided a hook 61 which is pivotable about a pivot pin or journal 60, this hook 61 being shown in FIGS. 6 and 7b in its closed position and in FIG. 7a in its open position. Hook 61 can be rocked by means of an eccentric 63 formed at a sturdy pin 62. This pin 52 extends essentially parallel to the pivot pin 60 and, as best recognized from the illustrations of FIGS. 7a and 7b, is equipped at its end with a transversely extending threaded bore 64 into which there is threaded the end of the clamping lever 38 provided with a bolt thread 65. This bolt thread or threading 65 terminates in a dull tip 66. As long as the tip 66 does not extend past the diameter or outer surface of the pin 62 the latter, and thus the eccentric 63 can freely rotate. As seen from FIG. 7b it is however possible to arrest the closed position of the hook 61 by threading the bolt threading 65 further through the threaded bore 64 until the tip 66 contacts an inclined surface 67 and thus presses the eccentric 63 with a still greater force against the hook 61, and, on the other hand, prevents any return rocking of the clamping lever 38 in the counterclockwise direction. From the foregoing it will be apparent that for shifting the holder block 35 along the rail 37 or for detaching such holder block from such rail two movements are required, namely, first of all threading of the clamping lever 38 out of the threaded bore 64 and only thereafter an upward rocking or pivoting of such clamping lever 38. As a result there is realized an extremely positive safeguard against unintentional shifting of the holder block 35 along the rail 37 and hence undesired shifting of the entire device. Additionally, in FIGS. 6, 7a and 7b there is illustrated a pin 68 secured to the holder block 35 and protruding upwardly from such holder block. The purpose of this protruding pin 68 will be explained more fully hereinafter in conjunction with the discussion of FIGS. 10 and 11.

From the showing of FIG. 1 it will be recognized that the overhang of the hinge or pivotable rod, namely the angle member 33, the stand 24, the end or terminal piece 21, the clamping head 14 up to the wound hook 11, i.e., the spacing thereof from the axis of the bore 151 in the holder block 35, can be considerable. Consequently, during use of the device torsional forces can be effective at the leg 34 which such leg or leg member 34 itself can readily withstand, yet however cannot be taken-up by the bore 151 containing the thrust sleeve 43 without considerably tightening the handwheel 58.

Thus, as illustrated in FIG. 10, in order to prevent any turning of the angle member 33 out of the once selected angular or rotational position with regard to the holder block 35, a sleeve member 69 is arranged to be easily displaceable but non-rotatable upon the leg or leg member 34. In the bore 70 of the sleeve member 69, which bore surrounds the leg 34 with a small amount of play, there is anchored a wedge or key 71 of substantially round cross-sectional configuration. This wedge or key 71 engages into the lengthwise groove 49 and thus prevents the sleeve member 69 from rotating relative to the leg 34. At the outside of the sleeve member 69 there is provided at its upper end a collar 72 which ensures for positive engagement of the sleeve member 69 through the hood 18. At the other end of the sleeve member or sleeve 69, and as best seen by referring to FIG. 11, there is formed a toothed rim 73 having, for instance, ten teeth and ten gaps. The spacing of the pin 68 from the axis of the bore 151 is selected such that the pin 68, as shown in phantom lines in FIG. 11, always fits into a gap between two neighboring teeth of the toothed rim 73.

During operation, initially the surgical retaining device is brought into the desired position along the operating table 36 by means of the clamping lever 38 and then secured in place. Thereafter, by lifting the sleeve member 69 there is adjusted the desired rotational position of the angle member 33 with respect to the holder block 35. Upon releasing the sleeve member 69 the latter slides downwardly along the leg 34 until one of the tooth gaps of the tooth rim 73 comes into engagement with the pin 68. If required, this engagement of a tooth gap of the toothed rim 73 with the pin 68 can be facilitated by exerting a slightly back and forth rocking movement at the leg 32. Then, by means of the handwheel 58 there is undertaken the desired elevational positioning of the angle member 33. Now, after the relevant surgical instrument, for instance the required wound hook 11, has been clamped at the clamping head 14, this instrument can be brought into the desired work position by releasing the handwheel 30 and then locked in such position.

It is to be observed that owing to the presence of the sterile hood member or cover 18 all of the manipulations for adjusting the work position of the wound hook 11 are accomplished through the hood member 18 at the relevant arresting or locking means, without unnecessarily contaminating with germs the device. Additionally, it will be appreciated from the above disclosure that the force which is to be exerted by the wound hook 11 can be applied by the surgeon in any random desired direction. There is only needed a suitable adjustment of primarily the pivotable stand 24.

At this point reference is now made to the schematic cross-sectional showing of a portion of the surgical retaining device illustrated in FIG. 12, portraying details of an exemplary embodiment of a pivotable stand 24 and, especially, the means for arresting or locking the joints. There will be recognized the rod 25, a portion of the rod 26 and the pin joint or hinge 27 arranged between these rods 25 and 26. The one respective end of the tubular-shaped rods 25 and 26 possesses a flanged edge 74 (there is only shown the flanged edge 74 of the rod 25) which engages about the associated ball 22. The ball 22 in turn rests in a socket 75 which is attached at one end of a thrust rod 76 which extends lengthwise through the tubular-shaped rod 25. The other end of the thrust rod 76 is provided with a slide element or block 77 exposed to the action of a pressure spring 78 supported in the rod 25. This pressure spring 78 strives to shift the thrust rod 76 and together therewith the socket 75 from the flanged edge 74, and thereby releases the ball 22. To the extent visible in the showing of FIG. 12, the same components are provided in the rod 26 as in the rod 25, and thus have been designated with the same reference characters, however to which there is also applied a prime marking. Since the construction of the components cooperating with the rod 26 correspond to those described above for the rod 25 the same have not been further illustrated in FIG. 12 to simplify the showing of the drawings.

Each of the rods 25 and 26 terminates at the region of the pin joint 27 in a respective hollow joint or hinge eyelet 79 and 80. The flat contacting hinge eyelets 79 and 80 are pierced by a hinge pin 81 carrying at one end threading 82 onto which there is threadably connected the clamping lever 31 and at the other end is supported, while interposing a plate spring or spring washer 83 or equivalent structure, at the hinge or joint eyelet 80. Secured to or formed at the hinge or joint pin 81 is a first conical element 84 and a second conical element 85 is mounted to be lengthwise displaceable upon the hinge pin 81. This conical element 85 in turn is supported by means of a pressure sleeve 86 at the clamping or tightening lever 31.

If the clamping lever 31 is tightened, then, both of the hinge or joint eyelets 79 and 80 are pressed against one another, i.e., the pin joint 27 is blocked. At the same time, however, due to the action of the conical elements 85 and 84 the sliding elements or blocks 77 and 77' respectively, are displaced outwardly against the action of the pressure springs 78 and 78' respectively, so that the corresponding socket 75 arranged at the end of the associated thrust rods 76 and 76' fixedly clamps the corresponding ball and thus also blocks or arrests the ball-and-socket joints. It will be readily understood that for the described pivotable stand there can be readily adjusted any random "brake position" between the completely locked and the completely released positions, so that the wound hook or the like can be positioned in any random desired location and without undertaking any further displacements blocked in such selected position.

While there are shown and described present preferred embodiments of the invention, it is to be distinctly understood that the invention is not limited thereto, but may be otherwise variously embodied and practiced within the scope of the following claims. Accordingly,

What we claim is:

1. A surgical retaining device for holding a surgical instrument in place, especially a wound hook, comprising:
   a holder block assembly including means for displaceably securing the surgical retaining device along a stationary guide rail;
   at least one instrument receiving element at which there can be inserted and fixedly clamped the surgical instrument;
   means for interconnecting the holder block assembly and the instrument receiving element with one another;
   said interconnecting means comprising:
   a double-arm pivotable stand, equipped with an intermediate pin joint arranged between the instrument receiving element and the holder block;
   said pivotable stand having a first end and a second end;
   a ball-and-socket joint for connecting said first end of said pivotable stand with the instrument receiving element;
   overhang arm means carried by said holder block including a first and second end portion;
   a further ball-and-socket joint for connecting the second end of the pivotable stand to said overhang arm means;
   said holder block assembly comprising:
   a fixed clamp jaw and a pivotable clamp jaw for engaging said rail; rotatable cam means for actuating said pivotable clamp jaw; means for rotating said cam means; a substantially vertical bore and a transverse bore intersecting said vertical bore; a thrust sleeve having a longitudinal bore displaceably arranged in said transverse bore; tightening means for displacing said thrust sleeve with respect to said vertical bore;
   said overhang first end portion being adapted to be introduced into said vertical bore and through said longitudinal bore to be blocked in its elevational position by displacement of said thrust sleeve by said tightening means; said first end portion comprising an outwardly open longitudinal groove;
   a displaceable sleeve member having a longitudinal bore surrounding said overhang first end portion; a key member secured within said sleeve bore and engaging said longitudinal groove of said overhang;
   said displaceable sleeve member comprising at its periphery a toothed rim, the space between two adjacent teeth of said rim being adapted to engage a pin secured to said holder block assembly and thus to block said overhang first end portion in its rotational position with respect to the holder block assembly.

2. The surgical retaining device as defined in claim 1, further including:
a hood member formed of a flexible sterilizable material secured at a part of the insert element;
said hood member enclosing said pivotable stand, said overhang arm means and said holder block.

3. The surgical retaining device as defined in claim 1, wherein:
said interconnecting means has a maximum of said three joints defined by said sequence of said ball-and-socket joint, said pin joint and said further ball-and-socket joint.

4. The surgical retaining device as defined in claim 1, wherein:
said holder block assembly permits adjustment of selected angular positions of said overhang arm means with respect to said holder block and also retains said overhang arm means in its selected angular position and also permits adjustment of the overhang arm means with respect to said holder block and fixes the selected elevational position of said overhang arm means; and said instrument receiving element including a clamping head having an opening for receiving an instrument shaft therein.

5. The surgical retaining device as defined in claim 1, further including:
means provided for said overhang arm means and coacting with said holder block to prevent inadvertent removal of said overhang arm means from said holder blocks.

6. The surgical retaining device as defined in claim 5, wherein:
said means preventing inadvertent removal of the overhang arm means from said holder block incorporates spring-loaded stop means.

7. The surgical retaining device as defined in claim 1, further including:
common means for conjointly selectively blocking and releasing the two ball-and-socket joints and said pin joint.

8. A surgical retaining device for holding a surgical instrument, especially a wound hook, in place comprising:
a holder block assembly adapted to be displaced and clamped along a stationary guide rail,
said holder block assembly comprising:
a fixed clamp jaw and a pivotable clamp jaw for engaging said rail;
rotatable cam means for actuating said pivotable clamp jaw; and
lever means for rotating said cam means;
said holder block assembly further comprising:
a substantially vertical bore and a transverse bore intersecting said vertical bore;
a thrust sleeve having a longitudinal bore displaceably arranged in said transverse bore, said longitudinal bore having the same size as said vertical bore;
threaded tightening means for displacing said thrust sleeve with respect to said vertical bore;
an overhang arm having a circular cross-section and a first and second end portion;
said first end portion being adapted to be introduced into said vertical bore and through said longitudinal bore and to be blocked in its elevational position by displacement of said thrust sleeve by said threaded tightening means;
said first end portion comprising an outwardly open longitudinal groove;
a sleeve member having a bore and longitudinally displaceably surrounding said first end portion;
a key member secured within said sleeve bore and engaging said longitudinal groove;
said sleeve member comprising at its periphery a toothed rim, the space between two adjacent teeth of said rim being adapted to engage a pin secured to said holder block assembly and thus to block said first end portion in its rotational position with respect to the holder block assembly;
said second end portion being connected to a double-arm pivotable stand equipped with an intermediate pin joint and having a first end and a second end;
a ball-and-socket joint for connecting the second end to said second end portion;
a ball-and-socket joint at the first end for connecting thereto a receiving element;
said double-arm pivotable stand comprising means for concurrently blocking said pin joint and said ball and socket joints at said first and second ends;
said receiving elements comprising means for releasably receiving and for blocking therein said surgical instrument.

* * * * *